(12) United States Patent
Ungerleider et al.

(10) Patent No.: US 10,099,031 B2
(45) Date of Patent: Oct. 16, 2018

(54) MECHANICAL DEVICE FOR SOOTHING AGITATED PATIENTS

(71) Applicants: Dorothy Ungerleider, Encino, CA (US); John Harrison Ungerleider, Brattleboro, VT (US)

(72) Inventors: Dorothy Ungerleider, Encino, CA (US); John Harrison Ungerleider, Brattleboro, VT (US)

( * ) Notice: Subject to any disclaimer, the term of this patent is extended or adjusted under 35 U.S.C. 154(b) by 157 days.

(21) Appl. No.: 14/960,972

(22) Filed: Dec. 7, 2015

(65) Prior Publication Data
US 2016/0158488 A1 Jun. 9, 2016

Related U.S. Application Data

(60) Provisional application No. 62/124,023, filed on Dec. 8, 2014.

(51) Int. Cl.
*A61M 21/02* (2006.01)
*A61H 7/00* (2006.01)
*A61M 21/00* (2006.01)

(52) U.S. Cl.
CPC ............ *A61M 21/02* (2013.01); *A61H 7/004* (2013.01); *A61H 2201/0142* (2013.01); *A61H 2201/0149* (2013.01); *A61H 2201/1207* (2013.01); *A61H 2201/5007* (2013.01); *A61H 2201/5048* (2013.01); *A61H 2201/5058* (2013.01); *A61H 2201/5097* (2013.01); *A61M 2021/0022* (2013.01); *A61M 2021/0027* (2013.01)

(58) Field of Classification Search
CPC .......... A61M 21/00–21/02; A61H 7/00–7/008; A01K 13/004; A01K 15/024–15/025
See application file for complete search history.

(56) References Cited

U.S. PATENT DOCUMENTS

| | | | | |
|---|---|---|---|---|
| 3,403,674 A * | 10/1968 | Alimanestiano | ....... | A61H 7/004 601/134 |
| 3,552,388 A * | 1/1971 | Zelenka | ................ | A61M 21/00 601/112 |
| 4,872,422 A * | 10/1989 | Della Vecchia | ..... | A01K 13/004 119/621 |
| 5,016,617 A * | 5/1991 | Tarlow | ................... | A61H 7/004 601/101 |
| 8,262,631 B1 * | 9/2012 | Macsovits | .............. | A61H 23/02 600/15 |
| 2002/0072692 A1 * | 6/2002 | Batula | ...................... | A47D 9/02 601/84 |
| 2006/0207518 A1 * | 9/2006 | Steffen | ................. | A01K 13/004 119/702 |
| 2007/0179414 A1 * | 8/2007 | Imboden | ............... | A61H 19/00 601/72 |
| 2015/0105608 A1 * | 4/2015 | Lipoma | ................ | A61B 5/6896 600/27 |
| 2015/0237827 A1 * | 8/2015 | Frost | .................... | A01K 13/004 119/601 |
| 2016/0136039 A1 * | 5/2016 | Spence | .................. | A61H 7/004 601/46 |

* cited by examiner

*Primary Examiner* — Thaddeus Cox
(74) *Attorney, Agent, or Firm* — C. John Brannon; Brannon Sowers & Cracraft PC

(57) ABSTRACT

A system for soothing an agitated patient, including a motor, a linkage operationally connected to the motor, an armature operationally connected to the linkage, and a lifelike hand connected to the armature. Energization of the motor enables the lifelike hand to move in a generally circular, rubbing motion.

8 Claims, 7 Drawing Sheets

MECHANICAL DEVICE FOR SOOTHING AGITATED PATIENTS

CROSS-REFERENCE TO RELATED APPLICATIONS

This patent application claims priority to U.S. provisional patent application Ser. No. 62/124,023, filed on Dec. 8, 2014.

TECHNICAL FIELD

The present novel technology relates generally to mechanical engineering and, more particularly, to biomechanical devices.

BACKGROUND

Some residents in Alzheimer's disease and dementia-care facilities exhibit severe agitation and unprovoked loud, aggressive outbursts, often generalized and without any specific target. These behaviors prove to be highly disturbing to other residents, and can set off a 'chain reaction' of agitation. It has been observed that a human hand, gently placed on the agitated patient's back and rubbed in a circular motion, can often soothe the patient. The soothing effect is enhanced by softly spoken, reassuring language, and the calming effect can be almost immediate, thus ending the physical and vocal outbursts.

The major drawback with this treatment strategy is that it is labor intensive; the caregiver is locked into providing the gentle, rubbing contact and thus cannot attend to any other patients while delivering the calming contact. Moreover, the outbursts often resume as soon as the rubbing contact is discontinued. Thus, there remains a need for an improved patient care strategy. The present novel technology addresses this need.

DETAILED DESCRIPTION

Figure 1:
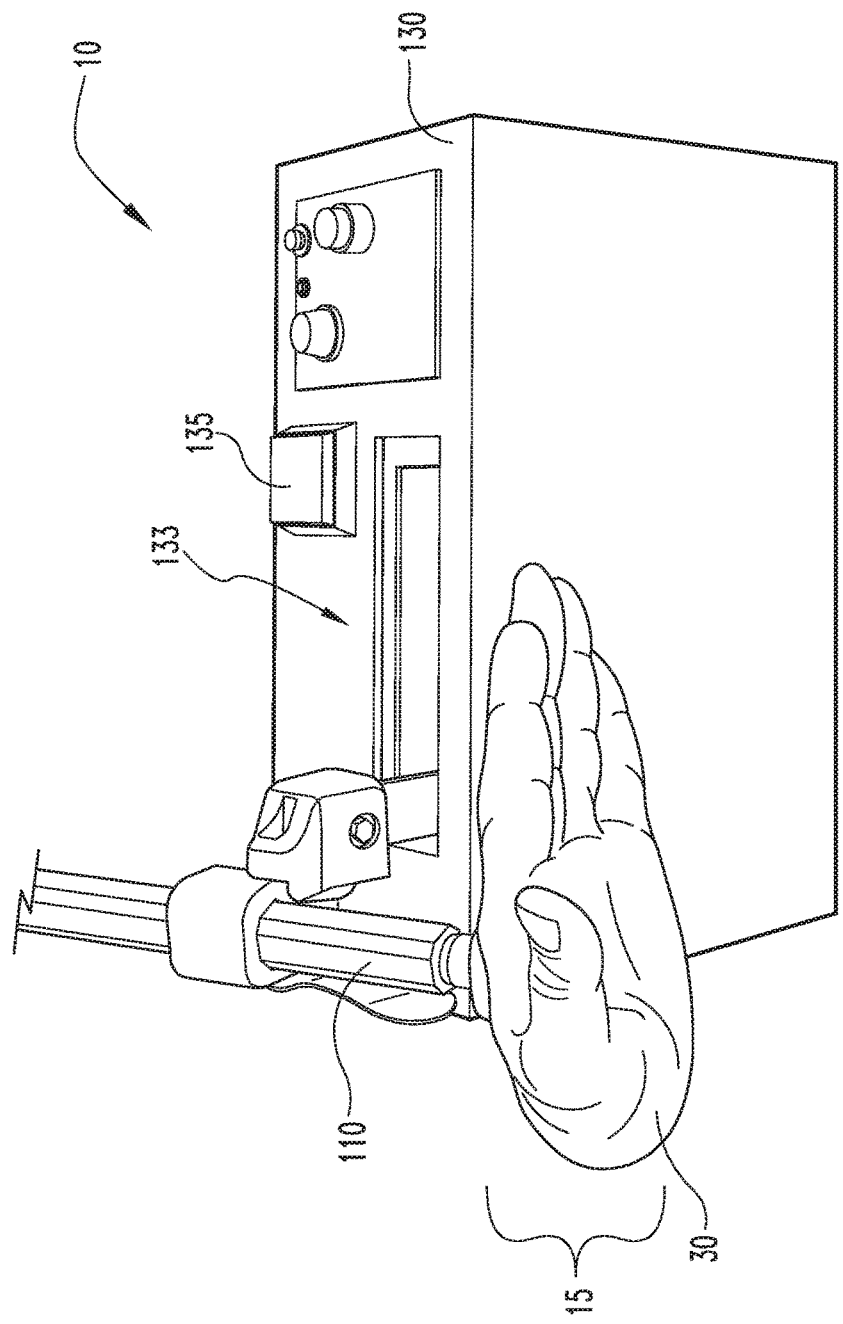
FIG. 1 is a perspective view of a first embodiment automatic mechanical soothing device of the present novel technology.
Figure 2:
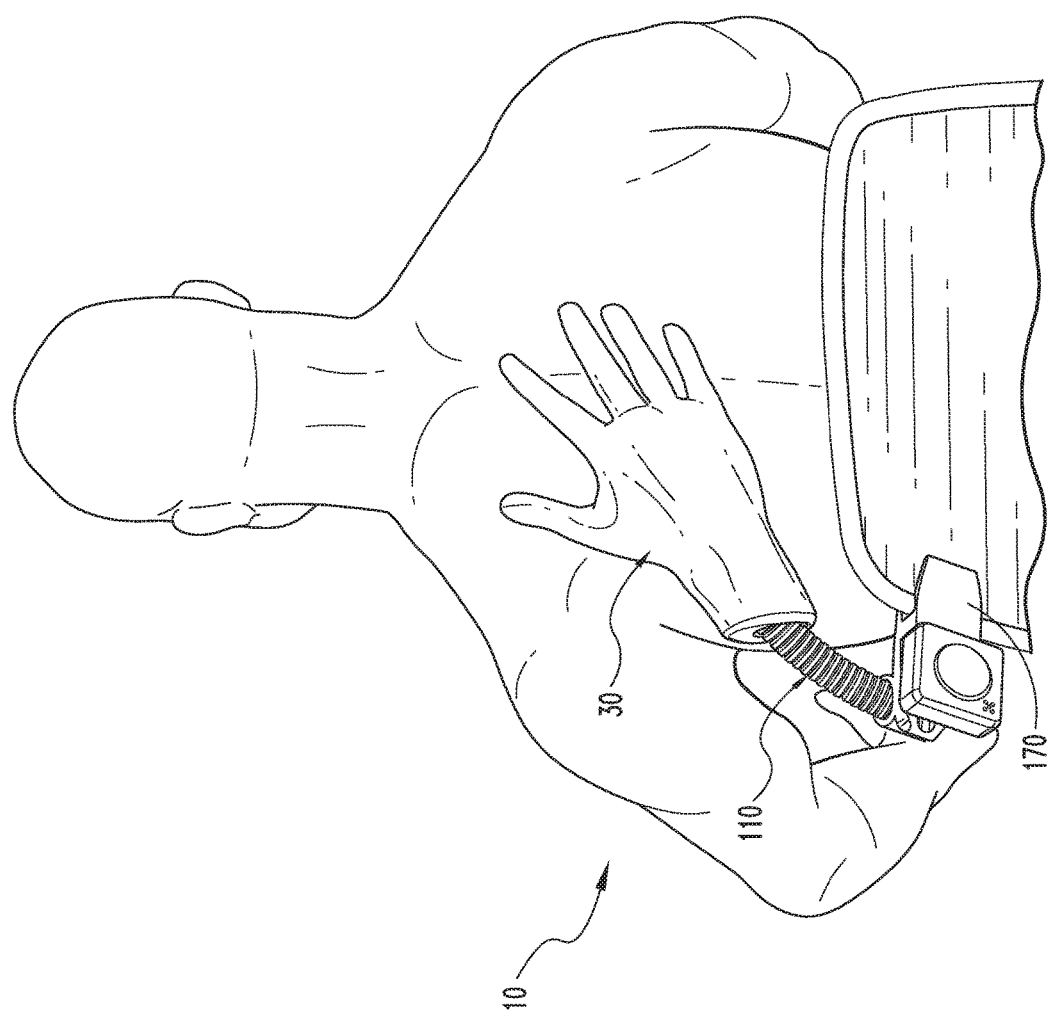
FIG. 2 is a partial perspective view of the embodiment of claim 1 in use with a patient.
Figure 3:
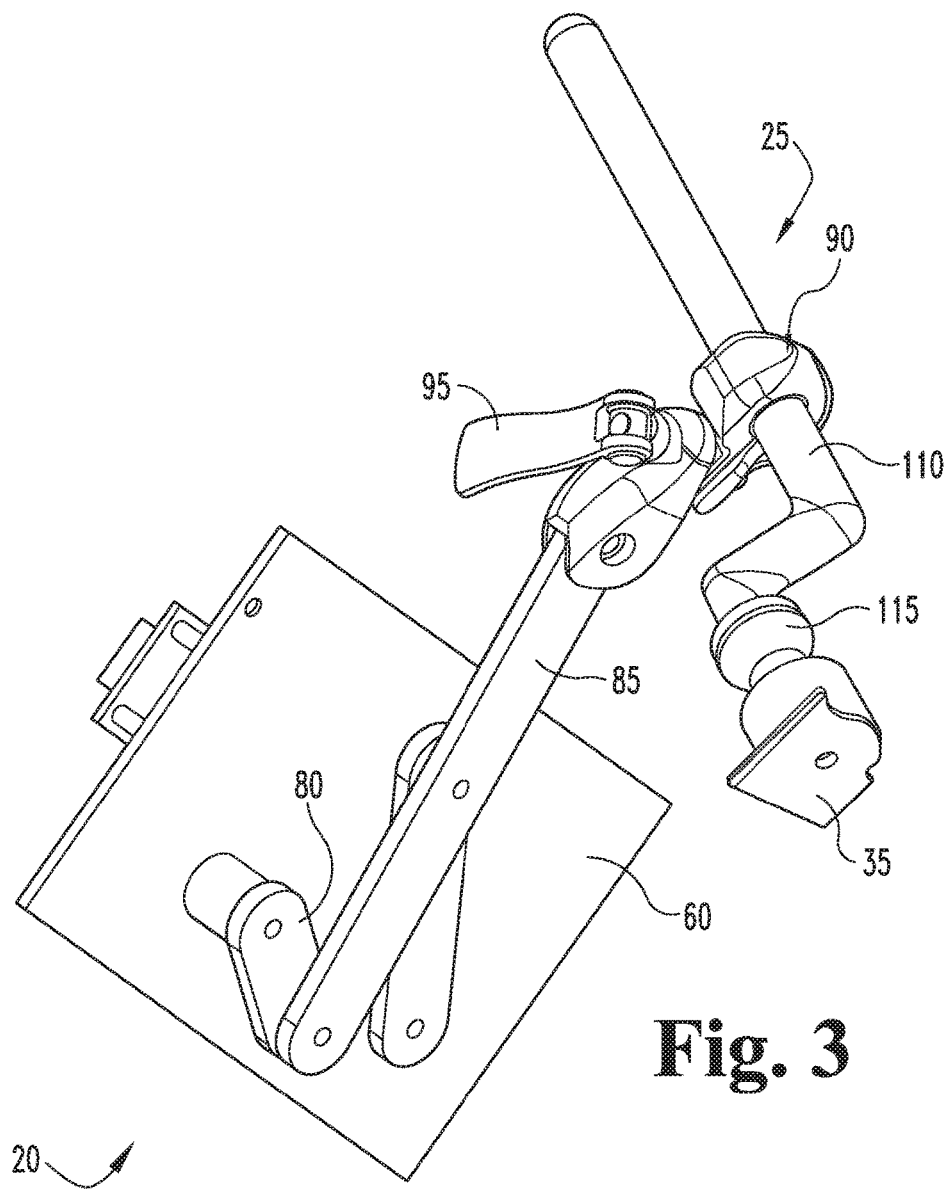
FIG. 3 is a perspective front view of the motor and linkage of the embodiment of FIG. 1.
Figure 4:
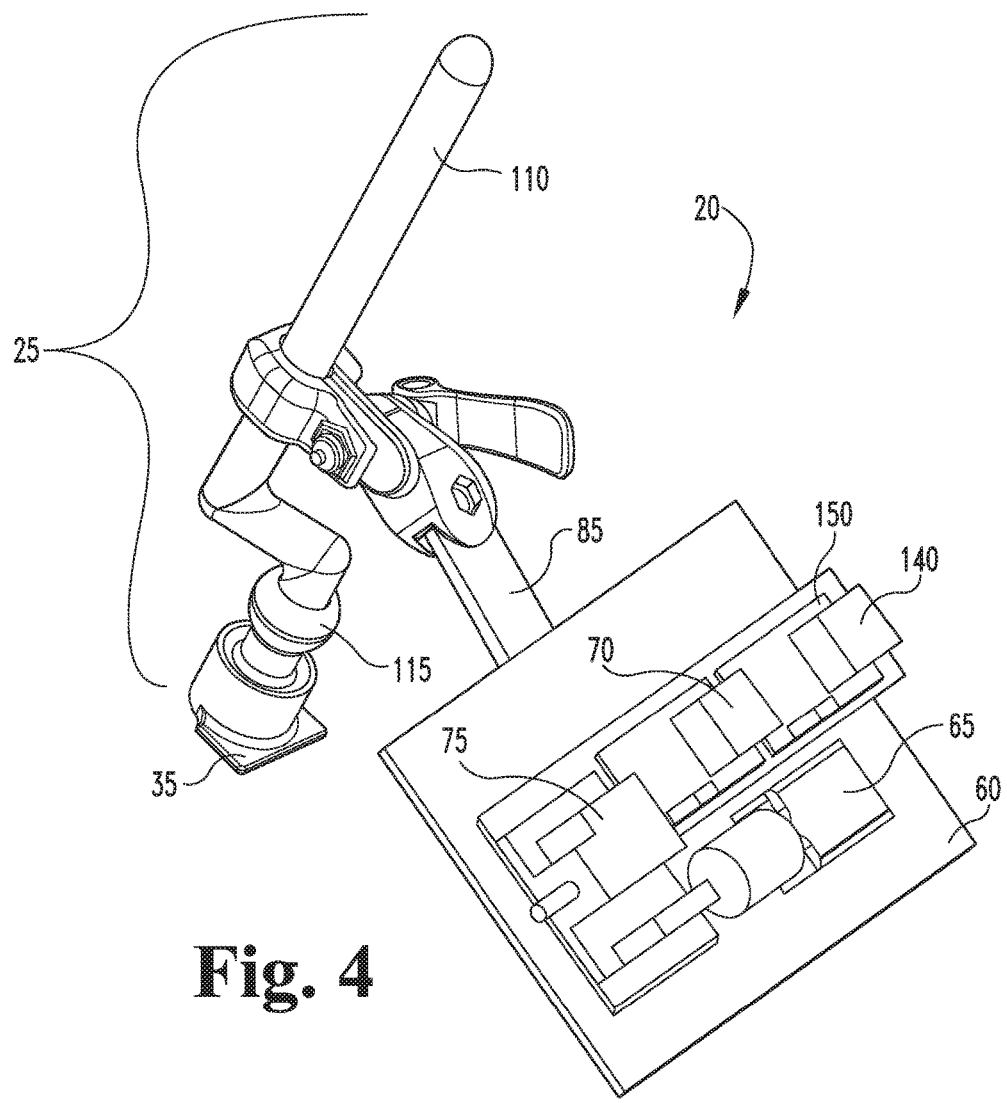
FIG. 4 is a perspective rear view of FIG. 3.
Figure 5A:
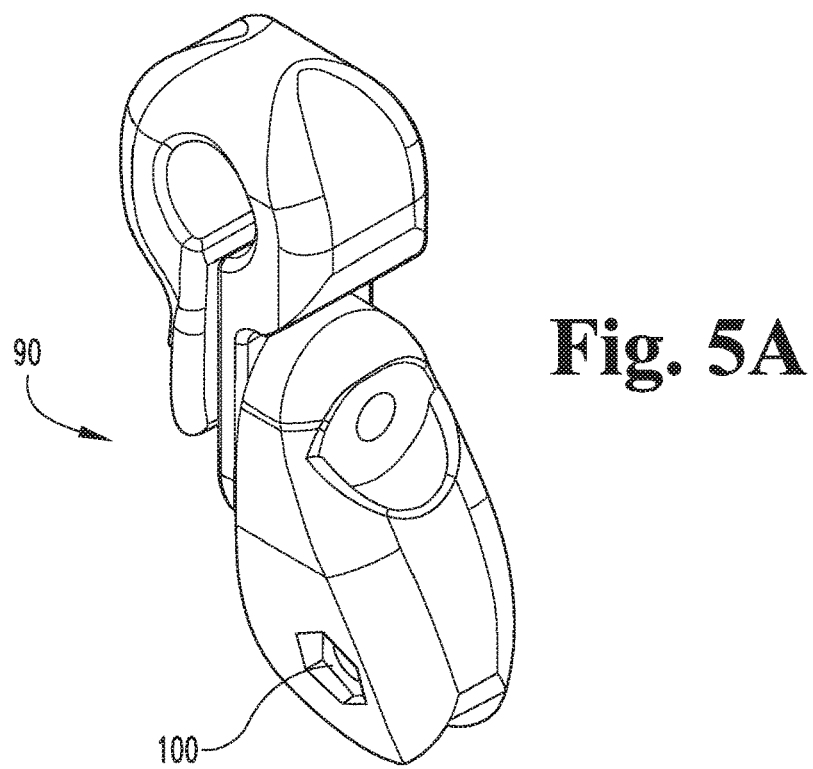
FIG. 5A is an isometric view of the shaft adjustment linkage of FIG. 3.
Figure 5B:
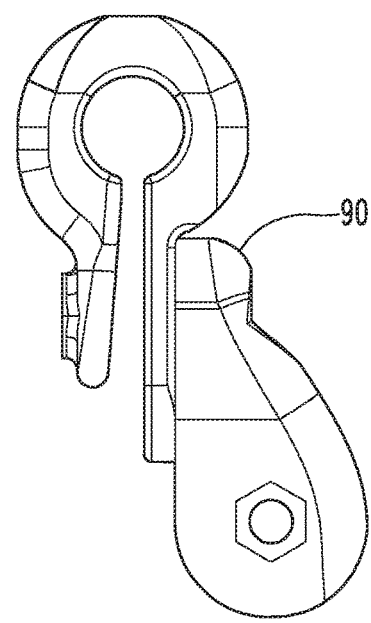
FIG. 5B is a front elevational view of FIG. 5A.
Figure 6A:
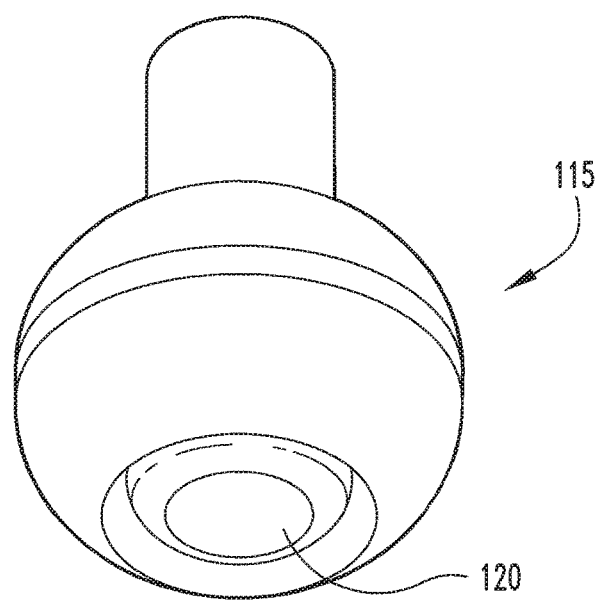
FIG. 6A is an isometric view of the shaft to hand adaptor of FIG. 3.
Figure 6B:
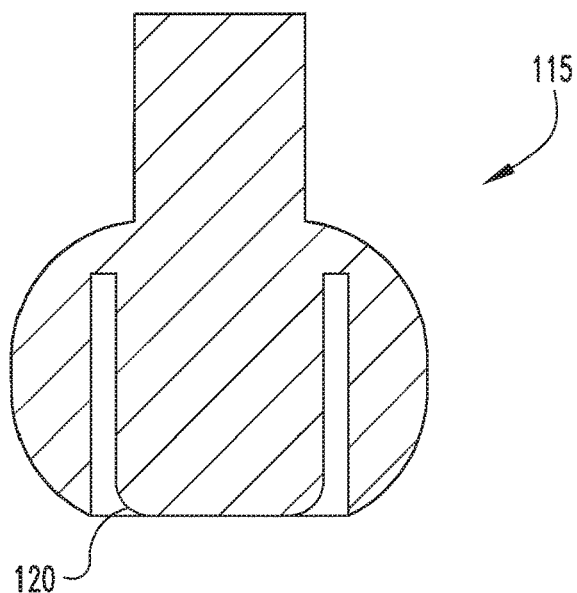
FIG. 6B is a front cutaway view of FIG. 6A.
Figure 7A:
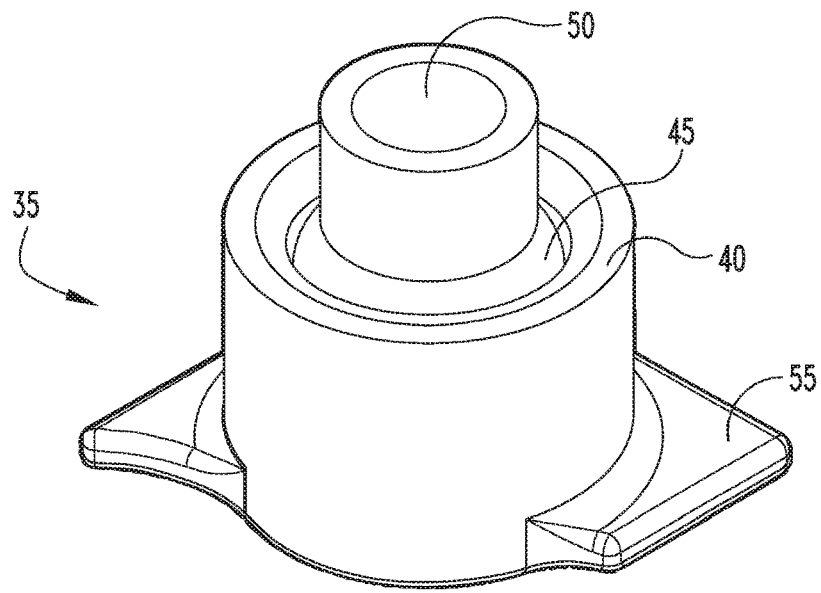
FIG. 7A is an isometric view of the ball joint insert of FIG. 3.
Figure 7B:
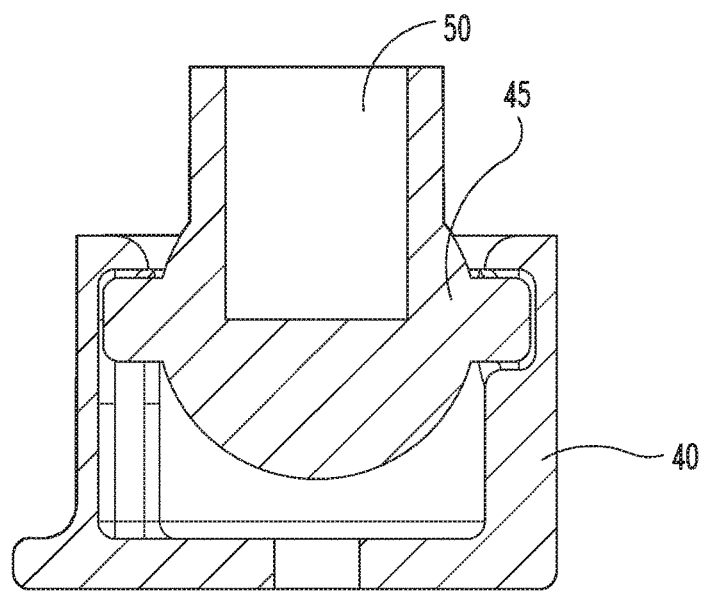
FIG. 7B is a front cutaway view of FIG. 7A.

For the purposes of promoting an understanding of the principles of the invention and presenting its currently understood best mode of operation, reference will now be made to the embodiments illustrated in the drawings. It will nevertheless be understood that no limitations of the scope of the invention is intended by the specific language used to describe the invention, with such alterations and further modifications in the illustrated device and such further applications of the principles of the invention as illustrated therein being contemplated as would normally occur to one ordinarily skilled in the art As illustrated in FIGS. 1-7B, the present novel technology relates to an automated system 10 for providing tactile relief to a distressed patient, such as a child or a patient suffering from Alzheimer's disease or like dementia. The system 10 includes a surrogate hand portion 15 and a base portion 20 operationally connected by an intermediate armature portion 25.

The surrogate hand portion 15 includes a lifelike artificial or mannequin hand 30 with a ball joint insert 35 disposed therein. The hand 30 may be made of any convenient material, such as plastic, rubber, silicone, foamed polymer or the like, and is typically formed around the ball joint insert 35. The ball joint insert 35 further includes a socket 40 with a ball joint 45 disposed therein for providing limited or restriction freedom of motion of the hand member 30, so as to better simulate the range of motion of a human hand extending from a wrist. The ball joint 45 typically includes a connector 50 for connecting to the armature portion 25. The hand 30 is typically made of a foamed polymer material that is more typically poured or otherwise molded around the ball joint insert 35. The insert 35 also includes a flange portion 55 extending from the socket 40 to provide greater surface area to anchor the insert 35 inside the hand 30.

The base portion 20 typically includes a plate member 60, upon one side of which a motor 65 and a controller 70 are typically mounted. The motor 65 is typically a D.C. electric motor, and the controller 70 is typically operationally connected to the motor 65. The controller 70 is typically a microcomputer or electronic controller, but may also simply be a relay switch or the like actuatable to energize the motor 65. Typically, the electronic controller 70 is Wi-Fi enabled so as to be remotely actuated and/or controlled, such as by a remotely located computer, a smart phone app, or the like.

In some embodiments, a pulse width modulator (PWM) 75 is operationally connected to the motor 65 to afford better control of the motor speed. The motor 65 is connected through the plate member 60 to a linkage 80 pivotably connected to the other side. The linkage 80 is typically a 4-bar linkage, and, as such, the linkage provides a range of full circular motion of the lifelike hand 30, although other convenient linkages may be selected. The linkage 80 typically includes an elongated member 85 that connects to a shaft adjust linkage member 90, such as by a quick-lock or like connector 95.

The linkage adjust member 90 accepts or otherwise connects to an elongated arm or shaft 110, which is part of the armature portion 25. The linkage adjust member 90 typically includes a built-in thumb screw 100 for adjustably securing the adjust member 90 to the arm 110. The shaft may be straight, or, more typically, include a bend or kink. In some embodiments the arm is rigid, while in others the arm 110 is partially flexible to lend itself to positioning adjustments. The shaft 110 terminates in an adaptor 115 rotatably connected to the shaft 110 and which includes a connector 120 matable with connector 50.

The base portion 20 may include a housing 130 for holding the plate member 60 and the gear mounted thereto. The housing 130 may also include enclosures or cubbies 133 for storing medicines, equipment, tools, or the like. The housing 130 may also include a power supply 135 connectable to the motor 65. The housing may also include an audio playback unit 140 having a speaker 145 and a memory 150 for storing prerecorded soothing messages, and may also include a telephone jack or interface 155 for operationally connecting to a cell phone. The housing 130 may also include a clip or fastener 170 for securing the system 10 within reach of the patient. In some embodiments, the system 10 includes a motion sensor, audio sensor, or the like for automatically actuating the motor 65 to drive the hand 30 in response to growing agitation of the patient.

In operation, the system 10 is secured within reach of a patient, such as clipped or fastened to the patient's chair. The hand 30 is placed against the patient's back and the motor 65 is energized. The hand 30 gently rubs or massages the patient's back in a generally circular pattern, typically in an irregular pattern as governed by the linkage assembly to more accurately simulate a person's natural rhythm. Likewise, the controller 70 may be programmed to alter or vary the speed and pattern of motion to follow a randomized or predetermined course while rubbing in a generally circular motion.

The playback unit 140 may likewise be energized to play soothing commentary and/or music.

When the system 10 is attached to a chair, bed, or the like, the controller 70 (either via remote or built-in options) drives the synthetic hand 30 so that the patient feels he is being soothed by a person.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

We claim:

1. A system for soothing an agitated patient, comprising:
   a motor;
   a linkage operationally connected to the motor;
   an elongated arm operationally connected to the linkage;
   a lifelike hand connected to the elongated arm;
   wherein energization of the motor enables the lifelike hand to move in a generally circular, rubbing motion;
   wherein the linkage provides a range of full circular motion of the lifelike hand; and
   further comprising a ball joint connector positioned inside the hand for connection to the elongated arm;
   wherein the ball joint connector operates to limit free motion of the hand relative the elongated arm.

2. The system of claim 1 and further comprising an electronic controller operationally connected to the motor.

3. The system of claim 2 and further comprising an audio playback unit operationally connected to the controller.

4. The system of claim 1 and further comprising an electronic controller operationally connected to the motor, wherein the electronic controller is remotely operated.

5. The system of claim 1 and further comprising a pulse width modulator operationally connected to the motor.

6. A system for soothing a distressed patient, comprising:
   a base portion;
   a hand portion; and
   an elongated arm connected to the base portion and the hand portion;
   wherein the base portion may be energized to provide an urging force;
   wherein when the hand portion receives the urging force from the base portion through the elongated arm, the hand portion moves in a predetermined circuit;
   wherein the base portion further includes:
     a plate member;
     an electric motor mounted to the plate member;
     an electronic controller mounted to the plate member and operationally connected to the electric motor; and
     a linkage mounted to the plate member and operationally connected to the electric motor;
     wherein energization of the electric motor urges mechanical movement of the linkage;
   wherein the elongated arm further comprises:
     an adjustment member operationally connected to the linkage;
     an elongated member mechanically connected to the adjustment member; and
     a first connection member connected to the elongated member; and
   wherein the hand portion further comprises:
     an artificial human hand; and
     a ball joint insert positioned within the artificial human hand and connectable to the first connection member;
     wherein the ball joint insert restricts the rotational freedom of the artificial human hand around the first connection member; and
   wherein movement of the linkage urges the hand portion to move in a generally circular pattern; and
   wherein the linkage provides a range of full circular motion of the artificial human hand.

7. The system of claim 6 and further comprising an audio playback unit operationally connected to the electronic controller.

8. The system of claim 6 and further comprising a clip operationally connected to the base portion for providing secure connection to a piece of furniture.

\* \* \* \* \*